United States Patent
Biegun et al.

(10) Patent No.: US 6,458,160 B2
(45) Date of Patent: Oct. 1, 2002

(54) KNEE PROSTHETIC WITH CAVITY IMPLEMENTED IN THE TROCHLEA

(75) Inventors: Jean-François Biegun, Chaumont (FR); Pascal Marceaux, Chaumont (FR)

(73) Assignee: Aesculap (FR)

( * ) Notice: Subject to any disclaimer, the term of this patent is extended or adjusted under 35 U.S.C. 154(b) by 0 days.

(21) Appl. No.: 09/781,792

(22) Filed: Feb. 12, 2001

(30) Foreign Application Priority Data

Feb. 24, 2000 (FR) .............................................. 00 2310

(51) Int. Cl.[7] .................................................. A61F 2/38
(52) U.S. Cl. ................................................. 623/20.27
(58) Field of Search .......................... 623/20.27, 20.28, 623/20.29, 20.31

(56) References Cited

U.S. PATENT DOCUMENTS 5,800,552 A   9/1998  Forte ............................ 623/20

FOREIGN PATENT DOCUMENTS

| WO | WO 89/06947 | 8/1989 | ............ A61F/2/38 |
| WO | WO 94/26212 | 11/1994 | ............ A61F/2/38 |

*Primary Examiner*—Paul B. Prebilic
*Assistant Examiner*—William H Matthews
(74) *Attorney, Agent, or Firm*—Renner, Kenner, Greive, Bobak, Taylor & Weber

(57) ABSTRACT

A complete prosthetic of the knee includes a femoral part (6) and a meniscus (3), with said femoral part (6) comprising at least one condyle (3) and a trochlea part, wherein said one or a plurality of condyles each have an external surface, the shape of which complements the respective upper surface of said meniscus (3) in order to obtain a congruence of said surfaces on at least part of the normal flexing range. At least one cavity is implemented in said trochlea such that the femoral part is blocked in its flexion by rotation in the case of negative angles beyond an inferior negative angle limit when the anterior upper edge of the meniscus comes to rest against said cavity.

7 Claims, 3 Drawing Sheets

KNEE PROSTHETIC WITH CAVITY IMPLEMENTED IN THE TROCHLEA

BACKGROUND OF THE INVENTION

1. Field of the Invention

The invention relates to a complete knee prosthetic, the type of which includes a tibia part comprising a support plate which is horizontal and fastened by means of appropriate anchoring means to the tibia which has been re-sectioned. It also includes a meniscus, which is generally in a plastic material and is put down on the tibia plate so as to be fastened or removable, and a femoral part which includes one or two condyles on the one side and a trochlea part on the other side. The present invention also relates to a femoral part of such a prosthetic.

2. Description of the Related Art

The external surface of the one or many condyles of the femoral part is generally spherical. When observed from a sagittal perspective, i.e. a perspective parallel to the axis of the tibia and/or to the axis of the femur when the knee is bent and thus also parallel to the pre-posterior axis, the shape of the condyles is an arc, the angle of which extends over the normal flexing range of a knee, i.e. zero to one hundred and twenty or one hundred and thirty degrees. The spherical surface of the condyle co-operates with the corresponding upper surface of the meniscus, which has a shape that is complementary to the spherical shape of the condyles, by means of a sliding action.

A prosthetic of this type is known, for instance from international patent application WO92/03108 of British Technology Group. The disadvantage of this type of prosthetic according to the prior art is that it is preferable to implement this prosthetic with conserving the posterior crossed ligament (PCL). In complete knee prosthetics according to the prior art, the femoral part can slide beyond zero degrees, i.e. beyond the vertical position defined by the tibia and the femur being parallel and thus into the range of negative angles of rotation. Said negative angles correspond to the fact that the tibia abnormally closes in on the femur from the front of the leg, as opposed to normally closing in on the femur from the back of the leg when one flexes the knees. This situation may eventually result in the dislocation of the meniscus or the femoral part, in the case of an implementation without conserving the posterior crossed ligament.

A complete prosthetic of this type is also known from European Patent 0 653 927 in the name of Walker, granted from PCT application WO94/26212. A cavity is implemented in the condyle to enable a perfect congruence when a flexing angle is null (knee extended). It is also preferable for this prosthetic to be implemented with conserving the posterior crossed ligament, for the same reasons as previously explained.

According to the invention, the above disadvantages are overcome by providing a complete knee prosthetic which can be implemented either with or without the posterior crossed ligament, and notably without the posterior crossed ligament, without said negative angles of rotation being permitted to reach values beyond minus five or minus ten degrees.

BRIEF SUMMARY OF THE INVENTION

A complete prosthetic of the knee according to the invention includes a femoral part and a meniscus, with said femoral part comprising at least one condyle and a trochlea part, wherein said one or a plurality of condyles each have an external surface, the shape of which complements the respective upper surface of said meniscus in order to obtain a congruence of said surfaces on at least part of the normal flexing range. At least one cavity and the relative emplacements are implemented in said trochlea part, the dimensions and shapes of said at least one cavity and the anterior upper edge of said meniscus being such that the femoral part is blocked in its flexion by rotation in the case of negative angles beyond an inferior negative angle limit.

A cavity is implemented in the trochlea part of the femoral part, which can rest on the anterior side against part of the upper edge of the meniscus according to a flexing angle of for instance of minus five degrees. The femoral part thus comes to rest against the abutment which is the meniscus by means of the cavity implemented in the trochlea and therefore cannot follow its rotation through to negative angles. Consequently, the complete knee prosthetic cannot flex in the wrong direction even though the posterior crossed ligament is not present. According to the prior art, it is indeed said posterior crossed ligament which prevents this rotation into negative angles. According to the invention, even if the posterior crossed ligament is not present anymore, this rotation into negative angles is prevented.

According to a preferred embodiment of the present invention, the value of said inferior negative angle limit is comprised between zero and minus ten degrees, preferably equal to minus five degrees.

According to a preferred embodiment of the present invention, said upper edge includes at least one shaped projection, in a sagittal perspective, complementary with said one or more of cavities such that said one or more projections come to rest against said one or more cavities.

According to a preferred embodiment of the present invention, said one or more projections have a height superior to the height of the posterior upper edges, relative to the flat base of the meniscus.

According to a preferred embodiment of the present invention, said one or more condyles are spherical in shape.

According to a preferred embodiment of the present invention, said condyles comprise two circular segments in a sagittal perspective, with the first of said segments being an intermediary circular segment with a greater radius and the second of said segments being an extremity circular segment with a smaller radius.

According to a preferred embodiment of the present invention, the cavity is implemented in the trochlea part at the level corresponding to an angle of ten to thirty degrees along the circular segment corresponding to the projection of the trochlea part in a sagiftal perspective, from the end of said condyles.

BEST MODE FOR CARRYING OUT THE INVENTION

The invention will now be described by way of example only with reference to the previously identified drawings.

Figure 1:
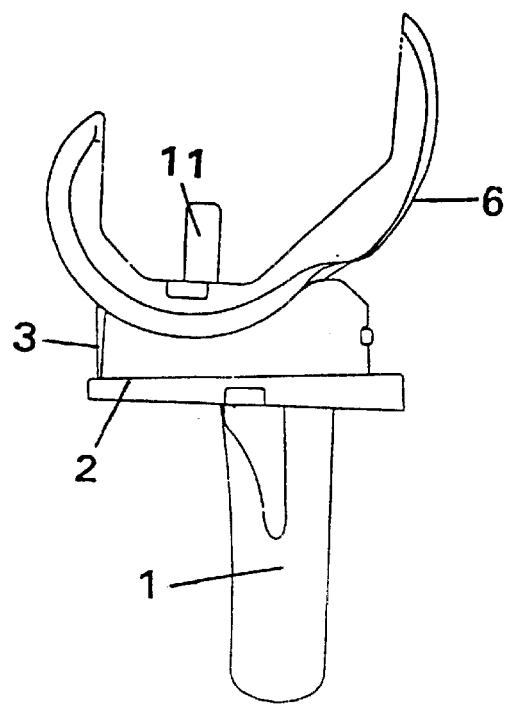
FIG. 1 is a cross-section of a knee prosthetic according to the invention corresponding to a knee in the extended position, i.e. with a flexing angle equal to zero degrees.

In FIG. 1, the flexing angle is the angle between the axis of the pin 11 and the axis 3 of the anchoring of the tibia part. In FIG. 1, this flexing angle is null. In the case of an anticlockwise rotation of the femur, relative to the tibia which is steady, the flexing angle is positive. For instance, in FIG. 3, the value of this angle is sixty degrees. In the case of a clockwise rotation of the femur, relative to the tibia which is steady, the flexing angle is negative. For instance the value of this angle is minus five degrees in FIG. 2.

A complete knee prosthetic, the position of which corresponds to an extended knee, is shown in FIG. 1. Said complete knee prosthetic includes a tibia part 1 comprising a tibia plate 2, stemmed from an anchoring axis 3, the purpose of which is to anchor itself in the tibia bone. An tibia insert 3 or meniscus in polyethylene material is resting on the tibia plate 2. Said tibia insert 3 co-operates with said tibia plate 2 by means of a tenon 4, fixated to said tibia plate 2 and a cavity 5 implemented in said tibia insert. The tibia insert can thus pivot relative to the axis of tenon 4 and perform medio-lateral and antero-posterior translatory movements within a set range of movements. Co-pending French applications Nos. 99 01 158 dated Feb. 2, 1999 and 99 08 632 dated Jul. 5, 1999 of the present assignee, may be usefully consulted for reference to a more detailed description of this part of the complete knee prosthetic, which is not part of the present invention. The complete knee prosthetic also includes a femoral part 6.

Said femoral part 6 includes two spherical condyles 7 and 8 separated by an inter-condyle clear interval, and a trochlea part 20. In a sagiftal perspective, i.e. a perspective both parallel to the axis of the tibia and parallel to the axis of the femur when the knee is bent, condyles 7 and 8 have a circular shape. Said circular shape comprises two circular segments side-by-side, a principal circular segment 9 and an extremity circular segment 10. Said extremity circular segment 10 extends over an angle of thirty to forty degrees whereas said principal circular segment 9 extends over an angle of eighty to ninety degrees. The radius of the secondary circle 10 is smaller than the radius of the principal circle 9. The radius of the principal circle 9 equals 1,25 times the radius of the secondary circle 10.

Figures 6, 7:
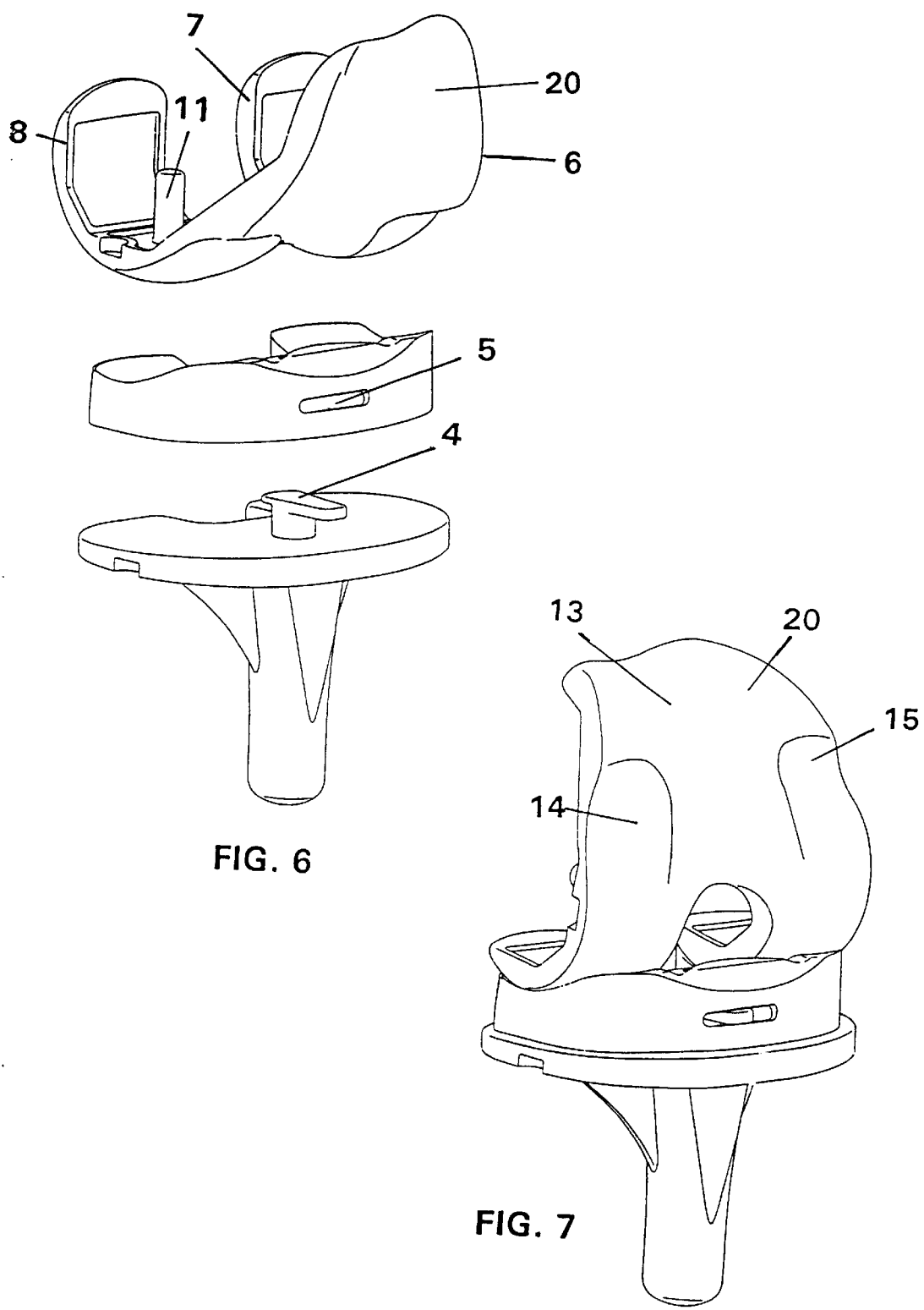
FIG. 6 is a cross-section in perspective of a knee prosthetic according to the invention.
FIG. 7 is another perspective view of the prosthetic shown in FIG. 6.

Two pins 11 (only one of which is shown in FIG. 6) ensure the femoral part is anchored in the femur bone. Said pin 11 defines the zero degree angle, which corresponds to the knee in the extended position, when it is parallel to tibia 1 as shown in FIG. 1.

Within the range of normal flexion of the knee, i.e. from zero degrees to one hundred and twenty or one hundred and thirty degrees, said condyles each co-operate with an upper surface 12 of the insert 3. In a sagittal perspective, said surfaces 12 also have a circular shape, with said shape complementing the spherical shape of condyles 7 and 8, and their radius is equal to the radius of the principal circle 9. A perfect congruence is thus obtained up to a flexing angle of circa eighty degrees.

The external resting surface of the trochlea part 20 extends beyond the condyles and the inter-condyle interval. A trochlean trajectory 13 is defined therein, the shape of which is a canal, as can be better observed in FIG. 7. In a sagittal perspective, the shape of this trochlean trajectory 13 is also a circle, notably with a greater radius than the radius of the principal circle 9.

Two cavities 14, 15 are implemented in the external surface of the trochlea part 20. Said cavities 14, 15 are for instance implemented by a cutting process.

Figure 2:
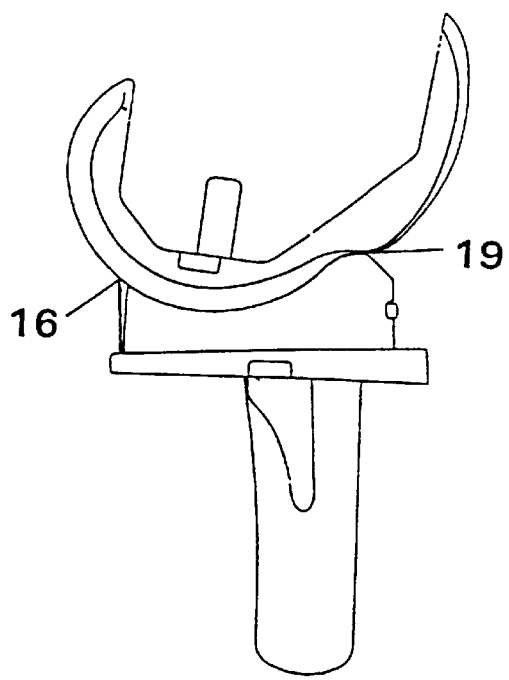
FIG. 2 is a cross-section of the same knee prosthetic as shown in FIG. 1 corresponding to a knee flexed according to the maximum negative flexing angle of minus five degrees.
Figure 3:
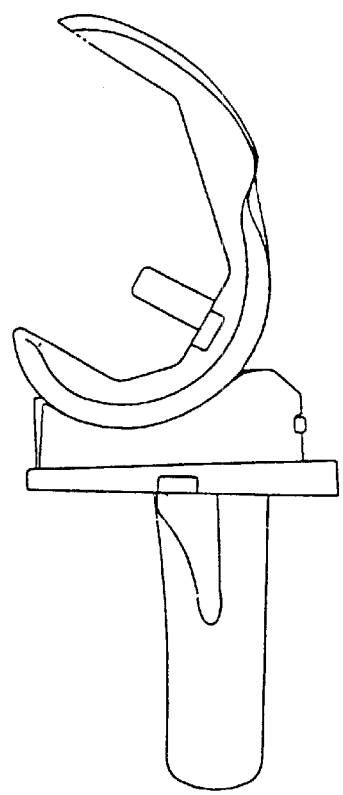
FIG. 3 is a cross-section of the same knee prosthetic as shown in FIG. 1 corresponding to a knee flexed according to a flexing angle of sixty degrees.

The tibia insert 3 or meniscus includes two posterior edges 16, 17, each of which demarcates one of the spherical upper surfaces 12 of said insert 3 on the posterior side. The tibia insert 3 is demarcated by an edge 18 on the anterior side. Said edge 18 includes two projections 19 which have a height greater than the height of posterior edges 16 and 17, relative to the perspective defined by the flat base 21 of tibia insert 3. In a sagittal perspective, said projections 19 are circularly curved and have a shape which complements the shapes of cavities 14, 15 such that, in the case of a flexion of the knee according to a set negative angle, i.e. a flexion of the knee of minus five degrees as shown in FIG. 2, the femoral part comes to rest against edge 18 and notably at the level of projections 19 by means of its cavities 14, 15 during its flexion by rotation. Any rotation beyond the set maximum negative angle, in the example minus five degrees, towards negative angles is thus prevented. It is therefore not necessary anymore to include the posterior crossed ligament in order to prevent the unwanted flexion into negative angles. The shape of cavities 14, 15 can be any or other shape, so long as said shape is complementary with the shape of projections 19 in a sagittal perspective of insert 3, such that cavities 14, 15 come to rest against projections 19.

The complete knee prosthetic shown in FIG. 2 is represented in the position depicting a flexion blocked to negative angles, as the angle between the tibia and the femur is equal to minus five degrees.

Figure 4:
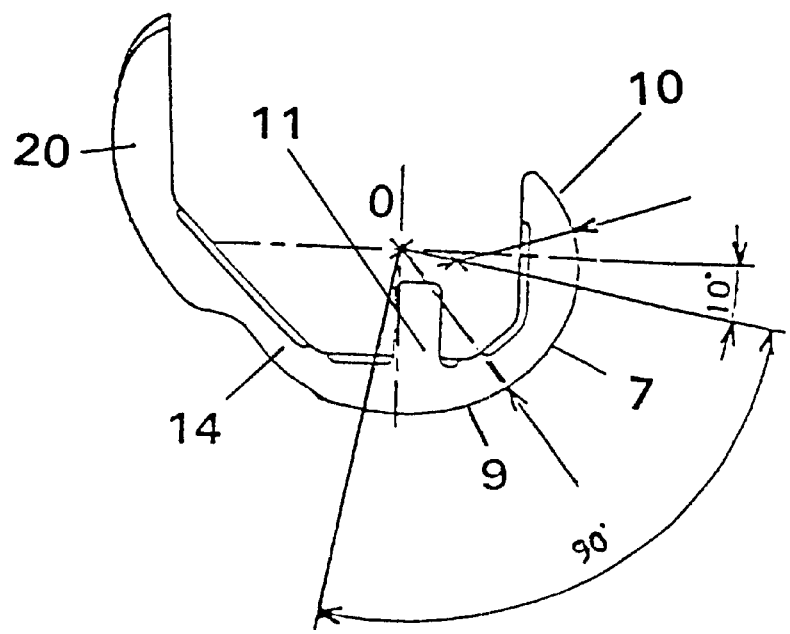
FIG. 4 is a cross-section in a sagittal perspective of the femoral part of the complete knee prosthetic according to the invention.
Figure 5:
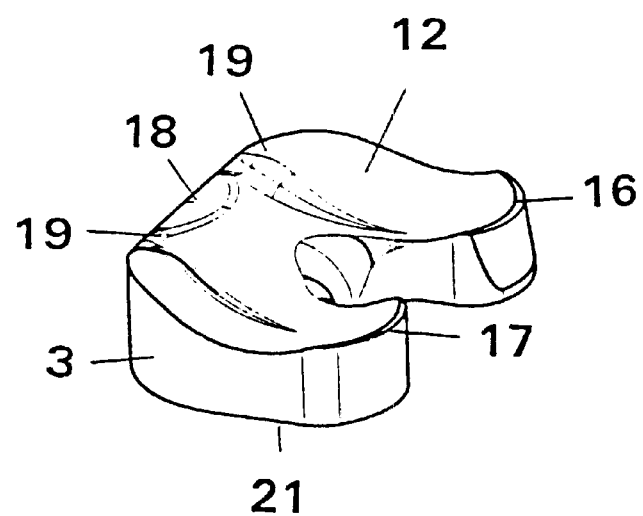
FIG. 5 is a perspective view of a tibia insert or meniscus of a complete knee prosthetic according to the invention.

A cross-section of the femoral part in a sagittal perspective is shown in FIG. 4. Circles 9 and 10 corresponding to condyles 7, 8 extend over a total angle of one hundred and thirty degrees and notably one hundred and twenty degrees from pin 11, in the positive trigonometric direction. Said angle corresponds to the range of normal flexion, with the condyles sliding over the meniscus as the femur flexes relative to the tibia.

Cavity 14 is implemented in the trochlea from the end of the condyles (OP axis), at a level corresponding to an angle of ten to thirty degrees along the circle corresponding to the projection of the trochlea part in the sagittal perspective. The height of the projections of edge 18 is such that the flexing angle is equal to minus five degrees when said projections rests against the cavity.

We claim:

1. A complete prosthetic of the knee including a femoral part and a meniscus having an anterior upper edge and a posterior upper edge, said femoral part including at least two condyles separated by an inter-condyle clear interval and a trochlea part starting from the trochlear end of the inter-condyle clear interval, wherein at least two cavities are implemented in said trochlea part, while leaving the condyles unaffected, the dimension and shapes of said at least two cavities and the anterior upper edge of said meniscus being such that the femoral part is blocked in its flexion by rotation in the case of negative angles beyond an inferior negative angle limit when the anterior upper edge of the meniscus comes to rest against said at least two cavities, wherein said anterior upper edge has a greater height than the height of the posterior upper edge, relative to the flat base of the meniscus.

2. A complete prosthetic of the knee as defined in claim 1, wherein said inferior negative angle limit has a value in the range of zero to minus ten degrees.

3. A complete prosthetic of the knee as defined in claim 1, wherein said inferior negative angle limit has a value of approximately minus five degrees.

4. A complete prosthetic of the knee according to claim 1, wherein said anterior upper edge includes at least one shaped projection in a sagittal perspective, complementary with one or more of said at least two cavities such that said at least one shaped projections come to rest against said one or more cavities.

5. A complete prosthetic of the knee according to claim 1, wherein said condyles are spherical in shape.

6. A complete prosthetic of the knee according to claim 1, wherein each of said condyles includes two circular segments in a sagittal perspective, with the first of said segments being an intermediary circular segment with a greater radius, and the second of said segments being an extremity circular segment with a smaller radius.

7. A complete prosthetic of the knee according to claim 6, wherein the at least two cavities are implemented in the trochlea part at a level corresponding to an angle of ten to thirty degrees along the circular segments corresponding to a projection of the trochlea part in a sagittal perspective, from the trochlear end of said condyles.

* * * * *